(12) United States Patent
Adams

(10) Patent No.: US 7,691,069 B2
(45) Date of Patent: Apr. 6, 2010

(54) METHOD, SYSTEM AND COMPUTER PROGRAM PRODUCT FOR PERFORMANCE MONITORING AND PLANNING

(76) Inventor: Joshua Adams, 41 Behrens Rd., New Hartford, CT (US) 06057

( * ) Notice: Subject to any disclaimer, the term of this patent is extended or adjusted under 35 U.S.C. 154(b) by 764 days.

(21) Appl. No.: 11/508,449

(22) Filed: Aug. 23, 2006

(65) Prior Publication Data

US 2007/0197920 A1 Aug. 23, 2007

Related U.S. Application Data

(60) Provisional application No. 60/710,395, filed on Aug. 23, 2005.

(51) Int. Cl.
*A62B 5/02* (2006.01)
(52) U.S. Cl. ...................................... 600/508
(58) Field of Classification Search .......... 600/508–509
See application file for complete search history.

(56) References Cited

U.S. PATENT DOCUMENTS 7,507,187 B2 * 3/2009 Dyer et al. ..................... 482/54

* cited by examiner

*Primary Examiner*—George R Evanisko
*Assistant Examiner*—Rex Holmes
(74) *Attorney, Agent, or Firm*—Cantor Colburn LLP

(57) ABSTRACT

A method for predicting athletic performance for a subject, the method comprising: obtaining first heart rate data for varying speed, constant incline running; obtaining second heart rate data for varying incline, constant speed running; determining a first power per change in speed at the constant incline; determining a second power per change in incline at the constant speed incline; predicting athletic performance in response to the first power and the second power.

15 Claims, 3 Drawing Sheets

Predict Ideal Race Pace

METHOD, SYSTEM AND COMPUTER PROGRAM PRODUCT FOR PERFORMANCE MONITORING AND PLANNING

CROSS-REFERENCE TO RELATED APPLICATIONS

This application claims the benefit of U.S. provisional patent application Ser. No. 60/710,395, filed Aug. 23, 2005, the entire contents of which are incorporated herein by reference.

BACKGROUND OF THE INVENTION

1. Field of the Invention

This invention relates to generally to athletic performance, and particularly to methods, systems and computer program products to track athletic performance, characterize athletic performance, predict specific performance, and plan athletic performance.

2. Description of Background

Systems exist for characterizing athletic performance that include techniques such as monitoring a subject's heart rate. Prior inventions have attempted to quantify the power required for human locomotion; however, they have focused on the theoretical power required to lift and propel the body. These inventions assume that all of the power used to lift the body into the "air" phase of a stride is lost upon landing. These prior systems do not accurately characterize the performance of a subject. Thus, there is a need in the art for a method to determine the net rate of energy expenditure (power) required for locomotion.

SUMMARY OF THE INVENTION

The shortcomings of the prior art are overcome and additional advantages are provided through the provision of a method for predicting athletic performance for a subject, the method comprising: obtaining first heart rate data for varying speed, constant incline running; obtaining second heart rate data for varying incline, constant speed running; determining a first power per change in speed at the constant incline; determining a second power per change in incline at the constant speed; predicting athletic performance in response to the first power and the second power.

System and computer program products corresponding to the above-summarized methods are also described and claimed herein.

Additional features and advantages are realized through the techniques of the present invention. Other embodiments and aspects of the invention are described in detail herein and are considered a part of the claimed invention. For a better understanding of the invention with advantages and features, refer to the description and to the drawings.

TECHNICAL EFFECTS

As a result of the summarized invention, technically we have achieved a solution which characterizes power expended by a subject to predict athletic performance.

BRIEF DESCRIPTION OF THE DRAWINGS

The subject matter which is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

Figure 1:
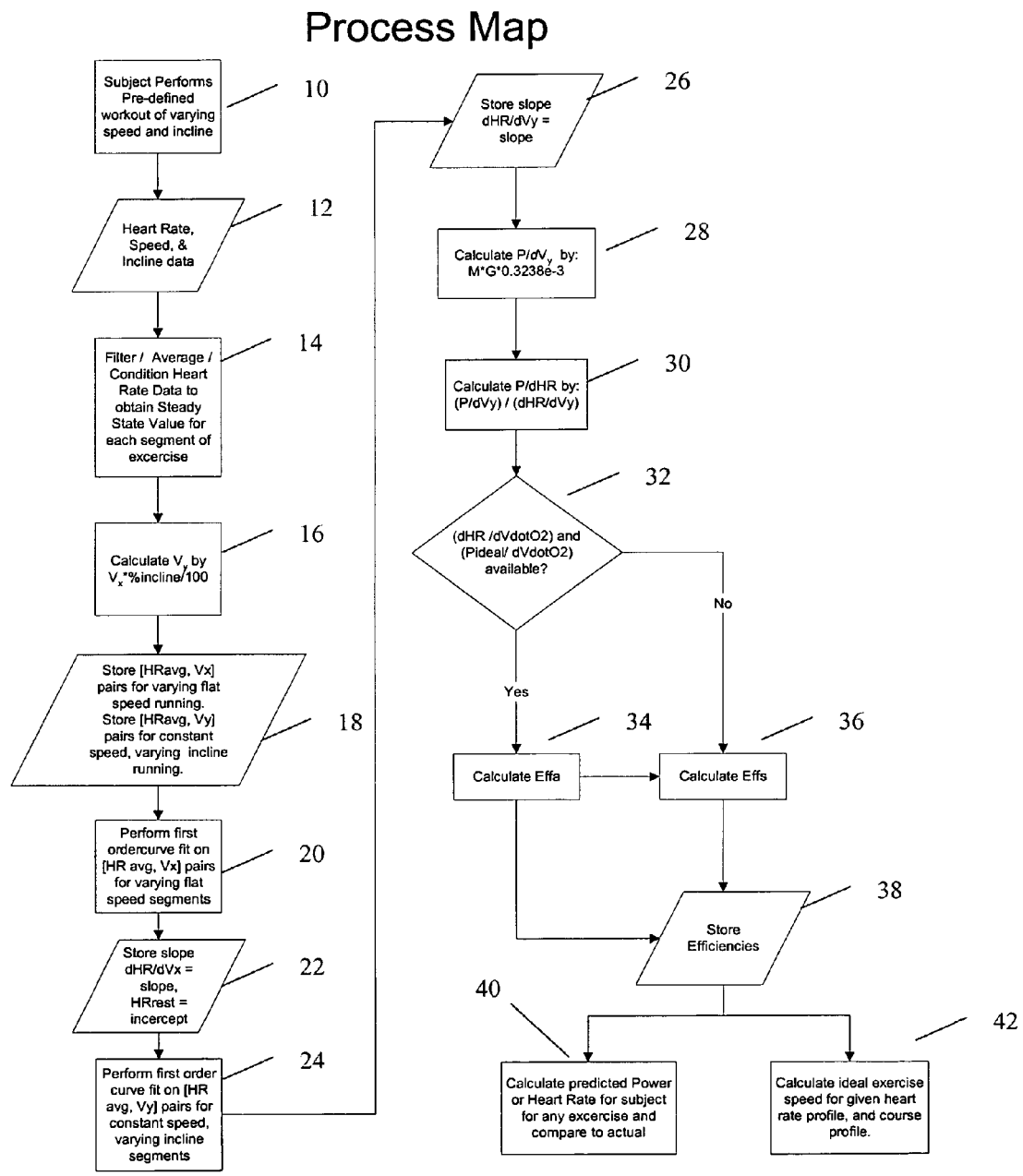
FIG. 1 illustrates one example of a process for characterizing athletic performance.

The detailed description explains the preferred embodiments of the invention, together with advantages and features, by way of example with reference to the drawings.

DETAILED DESCRIPTION OF THE INVENTION

Embodiments of the invention provide for determining and monitoring power used for human locomotion. Prior inventions have attempted to quantify the power required for human locomotion; however, they have focused on the theoretical power required to lift and propel the body. These inventions assume that all of the power used to lift the body into the "air" phase of a stride is lost upon landing. Embodiments of the invention include a method to determine the net rate of energy expenditure (power) required for locomotion.

Once the subject is characterized, a method and/or device can be used to calculate the power required for open road running. This information can be used to determine optimum race plans based on a racecourse profile (elevation) and a subject's characterization. The subject's performance can be optimized over the entire course.

The amount of power available through the body's chemistry can be determined based on the amount of oxygen ingested. By determining this in any of a number of available ways, the present invention can determine efficiency for the subject. The subject's efficiency can be tracked over time, and monitored for changes. These changes can be tracked and correlated to environmental, training, or personal variables.

The characterization of power required for running can be used to compare a single subject's performance on a plethora of courses. It can also be used to compare the performance of several subjects.

Embodiments of the present invention may be implemented in software that is used to track athletic performance, characterize athletic performance, predict specific performance, and plan athletic performance. The software can run on a personal computer, in a small handheld device (running computer watch), in a piece of training equipment, on the internet, or in any other computational environment, such as the program executing on a server accessed via a network. The software is stored on a computer readable medium accessible by a processor.

The following variables are used in this specification.

| Symbol | Definition | Units |
|---|---|---|
| Mr | Mass of Subject | Slugs |
| G | Gravitational acceleration | Ft/sec$^2$ |
| dy | Change in Altitude | Ft. |
| Vy | Rate of change in altitude | Ft/sec. |
| Vx | Flat ground running speed | Ft/sec. |
| E | Energy | Kcalories |
| P | Power | Kcalories/sec. |
| HR | Heart Rate | Beats Per Minute (BPM) |
| HRrest | Resting Heart Rate | BPM |
| VdotO2 | Rate of volumetric consumption of Oxygen | ml/sec |
| Effa | Aerobic system efficiency | unitless |

-continued

| Symbol | Definition | Units |
|---|---|---|
| Effs | Stride efficiency | unitless |
| ml | milliliters | |

Embodiments use a heart rate profile versus a course profile to characterize the true power output of the subject versus running conditions. A subject is characterized by determining the amount of power required to run on flat ground as a function of flat ground speed. This is accomplished by monitoring the subject's heart rate for a variety of speeds while running on flat ground. This is accomplished through the use of a treadmill so as to control a constant flat ground speed.

The present invention characterizes the usable aerobic energy contained in each heart beat. The energy required to change a subject's altitude is a basic calculation of:

$$E=(Mr)*(G)*(dy).$$

Power is defined as rate of change of energy. Therefore power required to change a subject's altitude depends on how fast the altitude is changed. The equation becomes:

$$P=(Mr)*(G)*(Vy).$$

A subject's heart rate is recorded during running at constant rate of change of altitude (constant incline on a treadmill) for a variety of inclines and/or declines on a treadmill. The term incline is used herein to refer to increases and decreases in altitude as the incline may have a positive or negative value. The heart rate data is analyzed to determine the steady state heart rate of the subject for a given rate of change of altitude. This can be accomplished through averaging, filtering, using endpoints, etc. Each "steady state" heart rate value corresponds to a rate of change of altitude value. A first order curve fit is performed on these pairs. The slope value of this fit defines the dHR/dVy, where d represents change in or delta. Because Vy is known, the mass of the subject is known, and G is known, the P/dVy is calculated easily:

$$P/dVy=(Mr)*(G).$$

Dividing:
(P/dVy)/(dHR/dVy).
Yields:
P/dHR.

This defines the useable power in each beat per minute of the subject's heart rate. The power required to run on flat ground is not trivial. Because the energy of a mass remains constant as it moves at constant elevation and constant speed, theoretically, no work is performed on the body. If no work is performed, no power is required. However, there are inefficiencies in human running. Power is required to run on flat ground.

Embodiments of the invention do not attempt to determine all of these losses, but rather characterizes the change in heart rate with a change in flat ground running speed. The subject is required to record heart rate while running a series of time periods at a constant rate (on a treadmill for consistency). The subject's heart rate is recorded during the exercise. The heart rate data is analyzed to determine the steady state heart rate of the subject for a given flat ground speed. This can be accomplished through averaging, filtering, using endpoints, etc. Each "steady state" heart rate value corresponds to a flat ground running speed value. A first order curve fit is performed on these pairs. The slope value of this fit defines the dHR/dVx. The offset value of this fit (e.g., where the fit curve crosses a speed of zero) is defined as HRrest. This is the Heart Rate required to provide oxygen for use by the body for other functions than running. This may or may not be the same as the subject's true resting heart rate. Because the amount of useable power per heart rate is determined as described above, we can calculate the power required per flat ground running speed:

$$P/dVx=(dHR/dVx)*(P/dHR).$$

Because oxygen intake varies directly with heart rate and the energy obtained by the human body though aerobic conversion in a given amount of oxygen is known, and a subject's rate of intake of oxygen can be determined at a plethora of athletic laboratories, the invention calculates subject's aerobic efficiency. The laboratory test can produce the value of the change in heart rate per the change in the rate of volumetric oxygen consumption (dHR/dVdotO2). The power converted to aerobic power per rate of oxygen consumed (Pideal/dVdotO2) is a constant for human aerobic power conversion. Embodiments calculate the P (applied power used to change elevation)/dHR. The present invention also calculates the subject's aerobic system efficiency by:

$$Effa=(Pideal/dHR)/(Papplied/dHR).$$

Embodiments also calculate stride efficiency. This is the power required to run on flat ground with respect to the power required to run in the vertical direction:

$$Effs=1-((P/dVx)/(P/dVy)).$$

This efficiency is a measure of how efficient a subject's stride is. The present invention stores and tracks the following calculated parameters: P/dVx, P/dVy, P/dHR, HRrest, Effa, and Effs for one or more subject's for comparison to an individuals performance over time or a many subjects performance at any given time, or many subjects over a period of time. Other variables can be used for comparison such as weather conditions, apparel, shoes, supplements, etc. Comparing a subjects stride efficiency by varying only one variable, such as shoes worn, and performing the same test will give the subject a quantitative measure of the impact of this one variable on his/her running. It may be used to determine the most effective shoe, or other variable for a particular subject.

FIG. 1 illustrates one example of a process for characterizing athletic performance. At step 10, the subject performs a pre-defined workout of varying speed and inclines to obtain heart rate data. The heart rate data, speed and incline data are collected as shown at step 12. At step 14, the heart rate data is split into segments and filtered and/or conditioned to obtain the steady state value for heart rate ($HR_{ss}$) of the given segment. The segments of the data may correspond to varying incline, varying speed at flat incline, etc.

The rate of change of altitude ($V_y$) is calculated at step 16 by the formula $V_y=V_x$ % incline/100. At step 18, the steady state heart rate values calculated in step 14 are paired with their corresponding $V_x$ for flat running segment and $V_y$ (as calculated in step 16) for inclined segments values, and these sets of data are stored. A first order curve fit is performed on the $HR_{ss}$ and $V_x$ pairs at step 20. At step 22, the slope of the curve fit performed in step 20 is stored as $dHR/dV_x$ and the intercept of the curve fit performed in step 20 is stored as $HR_{rest}$. A first order curve fit is performed on the $HR_{ss}$ and $V_y$ pairs at step 24. At step 26, the slope of the curve fit performed in step 24 is stored as $dHR/dV_y$. The slopes of these curves for flat running segments ($V_x$) and for inclined running segments ($V_y$) characterize the subject's performance for these two types of activities. Power used by the subject may now be determined.

The power required per foot/second of velocity in the vertical direction ($P/dV_y$) is calculated at step 28 by the formula $G*M*0.3238e-3$. At step 30, the power contained per heart rate (P/dHR) is calculated by the formula $(P/dV_y)/(dHR/dV_y)$. At step 32 if $dHR/dV_{dot}O_2$ Pideal/$dV_{dot}O_2$ data is available, move to step 34, if it is not available, move to step 36. This VO2 data may be available if the subject has had a VO2 max test, for example.

Figure 3:
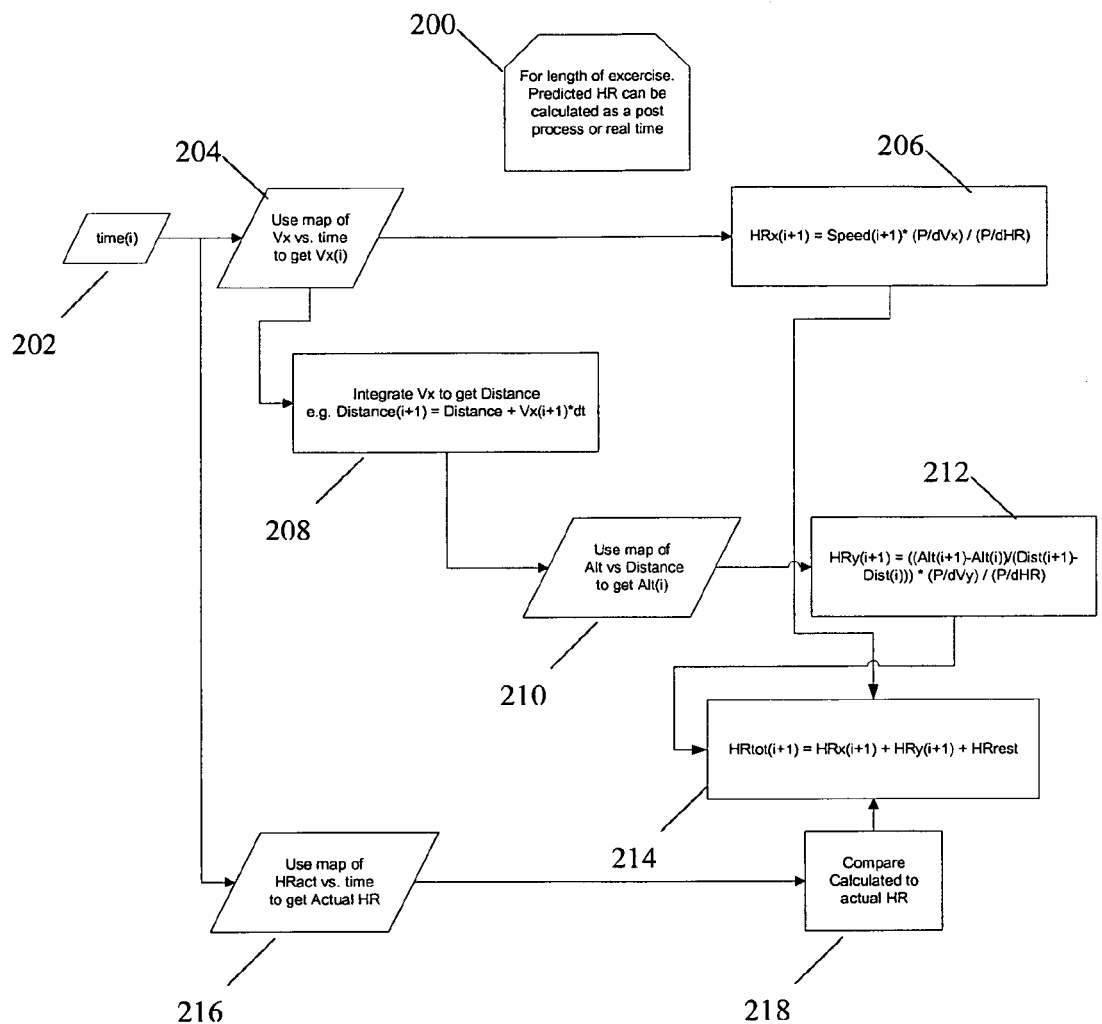
FIG. 3 illustrates one example of a process for comparing predicted heart rate to actual heart rate.

At step 34, aerobic efficiency is calculated by $(PO_2/dHR)/$(Papplied/dHR) if the VO2 data was available at step 32. Stride efficiency is calculated by $1-((P/dVx)/(P/dVx))$ at step 36. At step 38, these efficiencies calculated in steps 34 and 36 are stored. At step 40 the predicted power or heart rate for the subject for a given exercise is calculated and compared to the actual. This process is described in further detail herein with respect to FIG. 3. At step 42, the ideal exercise speed is calculated for a given course and an input heart rate or power profile. In other words, the user can enter a desired maximum heart rate and obtain a speed profile for a given course profile.

Once the subject's efficiencies are characterized, this data may be used to predict a subject's speed for a given course and a desired heart rate. For example, a subject may wish to run the Boston Marathon without exceeding a certain heart rate. The speed at which sections of the course should be run can be determined.

Embodiments use the parameters: P/dVx, P/dVy, P/dHR, and HRrest determined through the fitness testing defined above, as well as a given course distance, and course elevation profile to calculate the subject's ideal speed for a constant or varying power or heart rate. This ideal speed prediction can be used as a plan for an individual to run a race, for the comparison of an individual's fitness level over time, for the comparison of two or more athletes at a given time, or two or more athletes over time. It can also be used as a quantitative measure of the relative difficulty of one race-course to another. The algorithm for calculating this ideal speed is shown below.

Figure 2:
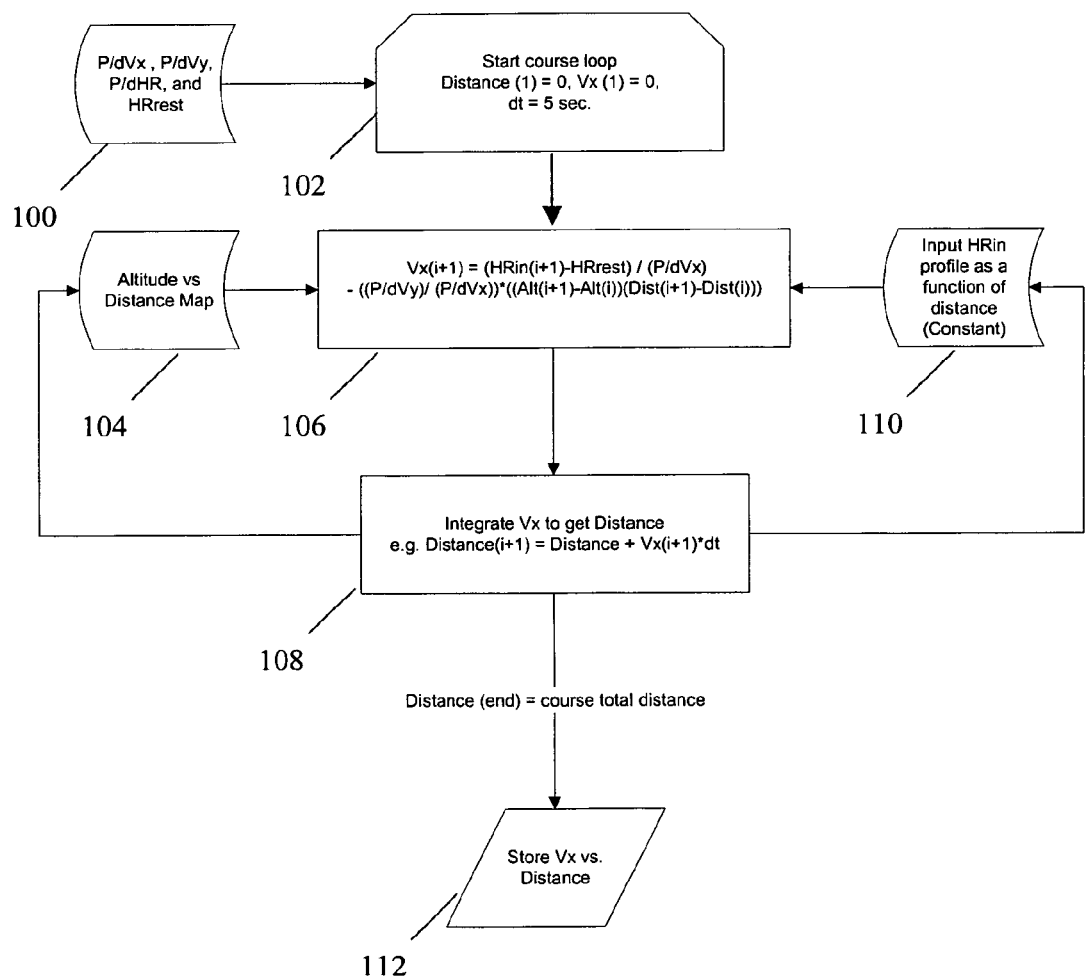
FIG. 2 illustrates one example of a process for predicting an ideal race pace.

FIG. 2 illustrates an exemplary process for predicting a pace for a race. At step 100, $P/dV_x$, $P/dV_y$, P/dHR, and $HR_{rest}$ are read in as inputs. The calculation loop is started with Distance(1)=0, Vx(1)=0, and dt=5 sec at step 102, where iteration, i, is equal to 1. At step 104 a courses altitude versus distance map is read in as an input. This course map describes the course inclines and declines with respect to distance.

The next Vx value (Vx(i+1)) is calculated by the formula:

$$(HR_{in}(i+1)-HR_{rest})/(P/dV_y)-((P/dV_y)/(P/dV_x))*(Alt(i+1)-Alt(i))/(Dist(i+1)-Dist(i))$$

at step 106, where Alt refers to altitude and Dist refers to distance. At step 108, the Vx(i+1) is integrated to get Dist(i+1). Dist(i+1) is fed to step 110 to calculate the HRin(i+2) value for the next iteration. It is also fed to step 104 of the next iteration. When the total course distance is reached, the Vx and Distance are recorded, and output at step 112. The computation at step 106 gives the user speed values for each section of a course in order to maintain a certain heart rate. This predicted speed may be stored in a portable device (sports wrist watch, heart rate monitor, etc.) so that the user has the speed data available while running a course. This allows the user to constantly match the computed speed to an actual speed to match the course prediction.

Embodiments use the parameters: P/dVx, P/dVy, P/dHR, and HRrest to compare predicted power output or predicted heart rate to actual power or actual heart rate. Heart rate and power are interchangeable just by the gain P/dHR. The speed profile, and the altitude versus distance profile of the given exercise is required as input. This can be done either as a post process or real time. The comparison can be used to evaluate the effectiveness of a training program, or the effects of environmental variables such as temperature or humidity on the subject's performance. The process to calculate predicted power or heart rate is shown below with reference to FIG. 3.

The process to predict race performance begins at step 200, where the iteration loop is set up based on the length of exercise and dt. The first time value is input at step 202. At step 204, Vx(i) is determined based on a device or read from a data file. The required heart rate for flat ground speed is calculated by $HRx(i+1)=Speed(i+1)*((P/dV_x)/(P/dHR))$. The next Distance value is calculated at step 208 by integrating Vx. At step 210, the present and next altitude are calculated from stored data, or read from the device. The heart rate required for the next step vertical velocity is calculated at step 212 by the formula $$(P/dV_y)/(P/dHR)*(Alt(i+1)-Alt(i))/(Dist(i+1)-Dist(i)).$$

At step 214, the next value for total heart rate is calculated by $HR_{tot}=HR_x+HR_y+HR_{rest}$. At step 216, the actual heart rate value is read from existing data or the device. For example, the user may have run a race and stored heart rate data in a portable device, such as a heart rate monitor. At step 218 the actual and predicted values are compared.

In another embodiment, the virtual race can be embodied in a computer game. In this game, the subjects enter their personal fitness data: P/dVx, P/dVy, P/dHR, and HRrest. A race-course is chosen. The subject's control the effort put forth (power applied) through a user interface. The effort is displayed as HR. The effects of heat, over exertion, energy deficit, and dehydration are manifested in the computer racer's performance.

As embodiments may be implemented in software, this provides a mechanism to track one or more subjects performance over time. The performance data may be stored remotely on a server accessible view a network (e.g., the Internet). Further, course data may be stored on the server allowing users to access the server and obtain predicted race performance for a variety of courses. This allows users to select road races and train appropriately. The performance of multiple users may be presented simultaneously for comparison. Users may also add notations to actual data to reflect changes in conditions (e.g., temperature, rain) or changes in equipments (e.g., shoes, energy gels, energy drinks). This data can reflect patterns in the user's performance.

The capabilities of the present invention can be implemented in software, firmware, hardware or some combination thereof.

As one example, one or more aspects of the present invention can be included in an article of manufacture (e.g., one or more computer program products) having, for instance, computer usable media. The media has embodied therein, for instance, computer readable program code means for providing and facilitating the capabilities of the present invention. The article of manufacture can be included as a part of a computer system or sold separately.

Additionally, at least one program storage device readable by a machine, tangibly embodying at least one program of instructions executable by the machine to perform the capabilities of the present invention can be provided.

The flow diagrams depicted herein are just examples. There may be many variations to these diagrams or the steps (or operations) described therein without departing from the spirit of the invention. For instance, the steps may be performed in a differing order, or steps may be added, deleted or modified. All of these variations are considered a part of the claimed invention.

While the preferred embodiment to the invention has been described, it will be understood that those skilled in the art, both now and in the future, may make various improvements and enhancements which fall within the scope of the claims which follow. These claims should be construed to maintain the proper protection for the invention first described.

What is claimed is:

1. A method for predicting athletic performance for a subject, the method comprising:
   obtaining first heart rate data for varying speed, constant incline running, the first heart rate data obtained from a heart rate monitor;
   obtaining second heart rate data for varying incline, constant speed running, the first second heart rate data obtained from the heart rate monitor;
   determining a power per change in speed at the constant incline;
   determining a power per change in incline at the constant speed incline;
   predicting athletic performance in response to the power per change in speed and the power per change in incline.

2. The method of claim 1 wherein determining the power per change in incline includes computing:

$$P/dV_y = G*Mr*0.3238e\text{-}3$$

where P is power, $V_y$ is rate of change in altitude, G is gravitational acceleration and Mr is mass of subject.

3. The method of claim 2 wherein determining a power per change in speed includes computing:
   power per change in heart rates as:

$$P/dHR = (P/dV_y)/(dHR/dV_y)$$

where $dHR/dV_y$ is determined from the second heart rate data for varying incline,
where HR is heart rate.

4. The method of claim 3 wherein determining a power per change in speed includes computing:

$$P/dVx = (dHR/dVx)*(P/dHR)$$

where $dHR/dVx$ is determined from the first heart rate data for varying speed, where Vx is flat ground running speed.

5. The method of claim 1 further comprising determining athletic efficiency for the subject, the predicting athletic performance being in response to the athletic efficiency.

6. The method of claim 5 wherein the athletic efficiency is aerobic efficiency computed as:

$$Eff_a = ((Pideal/dVdotO2)/((dHR/dVdotO2))/(Papplied/dHR)$$

where (Pideal/dVdotO2) is aerobic power per rate of oxygen consumed a constant for human aerobic power conversion;
($\Delta HR/dVdotO2$) is measured for the subject; and
(Papplied/dHR) is measured for the subject as applied power used to change elevation,
where P is power, VdotO2 is rate of volumetric consumption of oxygen and HR is heart rate.

7. The method of claim 5 wherein the athletic efficiency is stride efficiency computed as:

$$Eff_s = 1 - ((P/dVx)/(P/dVy))$$

where (P/dVx) is power to run on flat ground and (P/dVy) is power to run in a vertical direction,
where P is power, Vx is flat ground running speed and Vy is rate of change in altitude.

8. The method of claim 1 wherein:
   predicting athletic performance includes receiving a desired heart rate from the subject and a desired course; and computing a speed at which the subject runs the course to maintain the desired heart rate.

9. The method of claim 8 wherein:
   the speed is computed for multiple sections of the course.

10. The method of claim 8 wherein:
    the speed is calculated as $$(Vx(i+1)) = (HR_{in}(i+1) - HR_{rest})/(P/dV_y) - ((P/dV_y)/(P/dV_x))*(Alt(i+1) - Alt(i))/(Dist(i+1) - Dist(i))$$

wherein Vx is flat ground running speed, HR is heart rate, P is power, $V_y$ rate of change in altitude, Alt is altitude and Dist is distance.

11. The method of claim 1 wherein predicting athletic performance in response to the power per change in speed and the power per change in incline includes predicting athletic performance for multiple courses.

12. The method of claim 1 further comprising:
    for a second subject:
      obtaining first heart rate data for varying speed, constant incline running;
      obtaining second heart rate data for varying incline, constant speed running;
      determining a second power per change in speed at the constant incline;
      determining a second power per change in incline at the constant speed incline;
    predicting athletic performance of the second subject in response to the second power per change in speed and the second power per change in incline;
    comparing athletic performance of the subject and the second subject.

13. The method of claim 1 wherein predicting athletic performance is performed by a processor executing software is stored on a computer readable medium.

14. The method of claim 13 wherein the processor is in a sports wrist watch.

15. The method of claim 13 wherein the processor is in a heart rate monitor.

* * * * *